United States Patent [19]
Vander Stel et al.

[11] Patent Number: 5,100,199
[45] Date of Patent: Mar. 31, 1992

[54] BUILT-IN INFANT SEAT

[76] Inventors: Louis M. Vander Stel; Polly A. Vander Stel, both of 8601 - 60th Street, Alto, Mich. 49302

[21] Appl. No.: 652,861

[22] Filed: Feb. 8, 1991

Related U.S. Application Data

[63] Continuation-in-part of Ser. No. 534,473, Jun. 7, 1990, Pat. No. 5,026,118.

[51] Int. Cl.⁵ ............................................. B60N 1/12
[52] U.S. Cl. ................................. 297/238; 297/488
[58] Field of Search ............... 297/14, 112, 115, 238, 297/250, 487, 488

[56] References Cited

U.S. PATENT DOCUMENTS

| | | |
|---|---|---|
| 2,337,480 | 12/1943 | Logan . |
| 3,146,026 | 8/1964 | Berlin . |
| 3,166,355 | 1/1965 | Rocker . |
| 3,594,037 | 7/1971 | Sherman . |
| 4,230,366 | 10/1980 | Ruda . |
| 4,460,215 | 9/1984 | Chamberlain et al. . |
| 4,533,176 | 8/1985 | Wyttenbach . |
| 4,540,216 | 9/1985 | Hassel, Sr. . |
| 4,596,420 | 6/1986 | Vaidya .................. 297/238 X |
| 4,664,443 | 5/1987 | Casale .................. 297/238 |
| 4,690,455 | 9/1987 | Bailey et al. . |
| 4,722,568 | 2/1988 | Irvin ..................... 297/238 |
| 4,749,229 | 6/1988 | Dorto . |
| 4,756,573 | 7/1988 | Simin et al. . |
| 4,900,086 | 2/1990 | Steward . |
| 4,902,069 | 2/1990 | Lehnert . |
| 4,943,112 | 7/1990 | Law ....................... 297/238 |
| 4,986,600 | 1/1991 | LeBlanc et al. ......... 297/112 X |
| 5,026,118 | 6/1991 | Vander Stel et al. ..... 297/238 |

FOREIGN PATENT DOCUMENTS

| | | |
|---|---|---|
| 156836 | 9/1984 | Japan . |
| 2023415 | 1/1980 | United Kingdom . |

*Primary Examiner*—Peter R. Brown
*Attorney, Agent, or Firm*—Price, Heneveld, Cooper, DeWitt & Litton

[57] ABSTRACT

A seating unit for accommodating an adult in a seated position has a child restraint seat convertible from a position stored within the back of the adult seat to a position for holding and restraining a child. The child restraint seat has a generally U-shaped restraint bar member which extends horizontally from the seat back in an open position and which pivots about the ends of the legs to a vertical closed position, wherein the restraint bar lays flush with the forward surface of the seat back. The child seat also has a seat cushion portion which pivots about its lower end to lay horizontally in the open position upon the adult seat and which pivots vertically to nest between the legs of the restraint bar and lay flush in the seat back in the closed position. A top cushion extends between the stored restraint bar and the top of a high back style seat. The top cushion is flipped over the top of the seat back for child use.

30 Claims, 3 Drawing Sheets

BUILT-IN INFANT SEAT

CROSS-REFERENCE TO RELATED APPLICATION

The present application is a continuation-in-part of the copending patent application Ser. No. 07/534,473, filed June 7, 1990, now U.S. Pat. No. 5,026,118 issued June 25, 1991.

BACKGROUND OF THE INVENTION

The present invention relates to child restraint seats. Such seats are most widely known in use with automobiles. However, the present invention is also applicable to vehicles generally, such as busses, planes, trains and boats for example, and to theater seating and the like.

In typical use in automobiles for example, a child restraint seat is a bulky, rigid apparatus into which a child is strapped and which is fastened in a seating position in a car. Because the devices are bulky and are bothersome to remove and replace, child restraint seats are typically left in place in the car for the child's use. Only when circumstances necessitate the use of the seating position by an adult is the child seat generally removed from the car. Child restraint seats are thus seen as somewhat of a necessary nuisance, typically reserved for use in cars and seldom used in other types of vehicles or with other types of seating. While social acceptance and legislative requirements for the use of child restraint seats in cars is somewhat commonplace, there is also social and legislative interest in requiring their use in other vehicles, including busses, planes and trains.

While the desirability of an adult seat which is convertible to a child restraint seat is apparent, attempts to supply this need have had their own limitations and problems. U.S. Pat. No. 4,749,229 issued to Dorto on June 7, 1988, for example, discloses a device which inherently limits its utility by creating an overhead obstruction to a child who uses the seat. This requires the child to be of sufficiently small size to sit within a recessed area in the back of an adult seat. Other devices, such as are disclosed in U.S. Pat. No. 4,664,443, issued to Casale on May 12, 1987, for example, are impractical because they require an excessive volume of space.

SUMMARY OF THE INVENTION

The present invention addresses these problems with a practical convertible seating unit for accommodating an adult in a seating position and having an integral child restraint seat stored within the back of the adult seat. A child seat of the present invention includes two portions of the adult seat back which pivot forward to form a child seat cushion and a restraint bar and which pivot closed to form a smooth back support for an adult seating position.

In one aspect of the invention, the restraint bar portion generally resembles an inverted U in the closed position with a bight portion positioned to form the top edge of the adult seat back. Thus, a height restricting portion of the back does not remain when the child seat is deployed. The child seat cushion portion folds into a closed position to nest inside the closed restraint bar portion and forms the mid and lower back support for the adult seating position.

In another aspect of the invention, the child restraint bar and seat cushion are mounted to a framework such that the seat cushion can be moved forwardly, inclining the child seat back and providing a reclined seating position for the child.

In another aspect of the invention, a removable top cushion is used between the closed restraint bar and the top edge of the adult seat back when a high back adult seat style is used or when extending the restraint bar to be flush with the top edge of the adult seat back is impractical.

These and other objects, advantages and features of the present invention will become apparent upon review of the following specification in conjunction with the drawings.

DESCRIPTION OF THE PREFERRED EMBODIMENT

Figure 1:
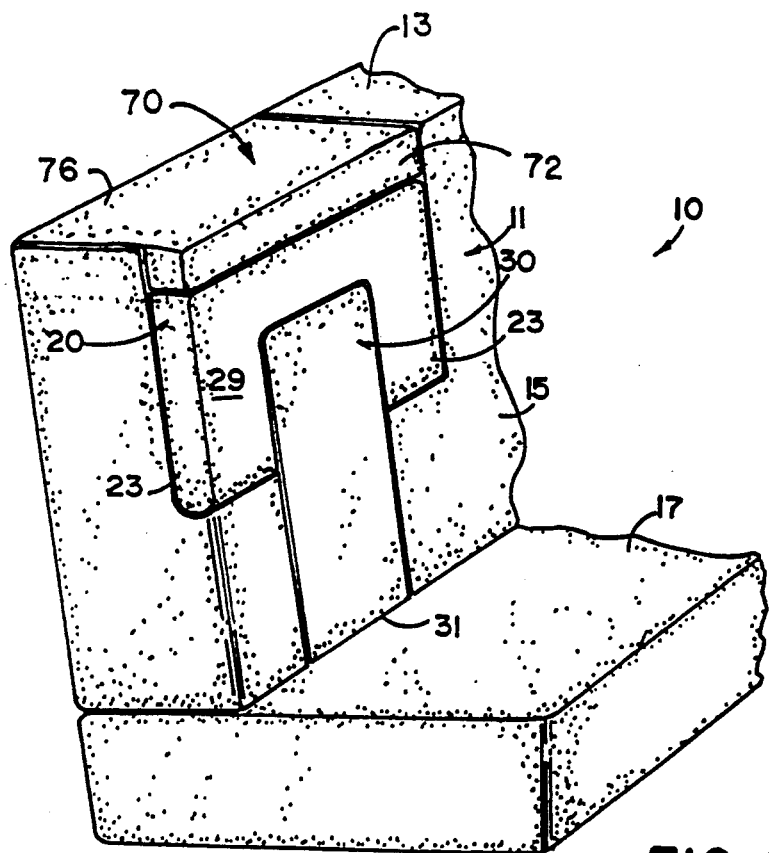
FIG. 1 is a perspective view of a seat according to the invention in the closed position.
Figure 2:
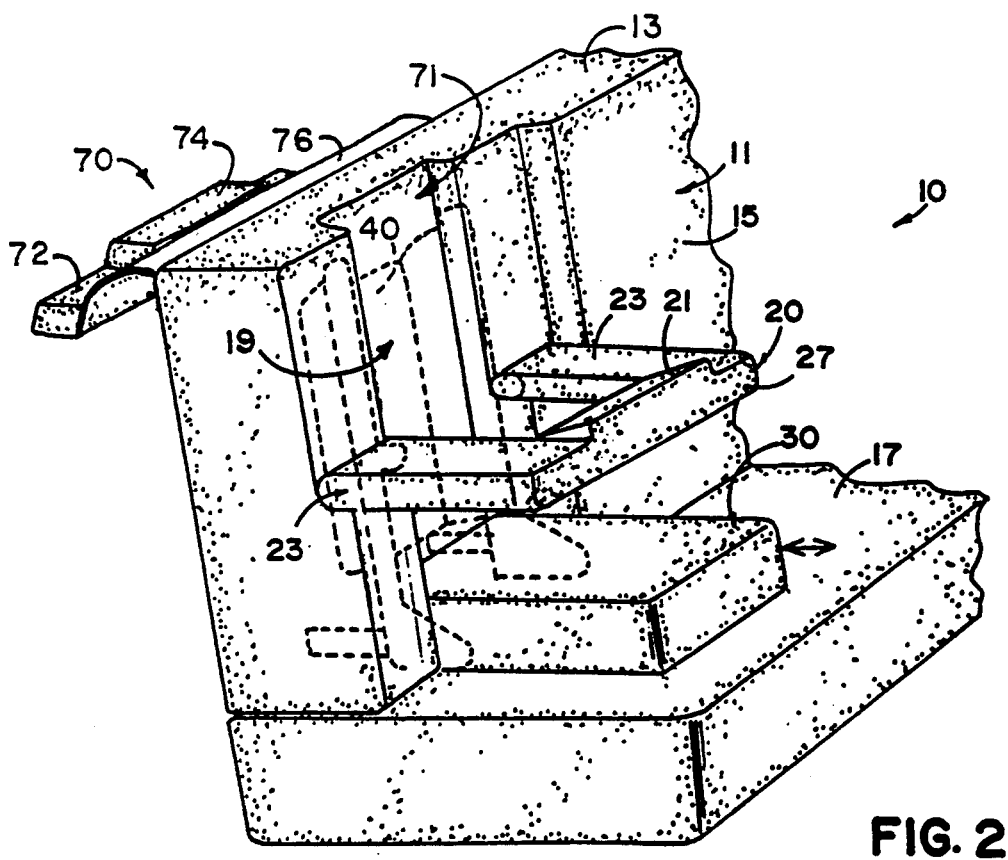
FIG. 2 is a perspective view of the seat of FIG. 1 in the open position with structural framework shown in phantom.
Figure 3:
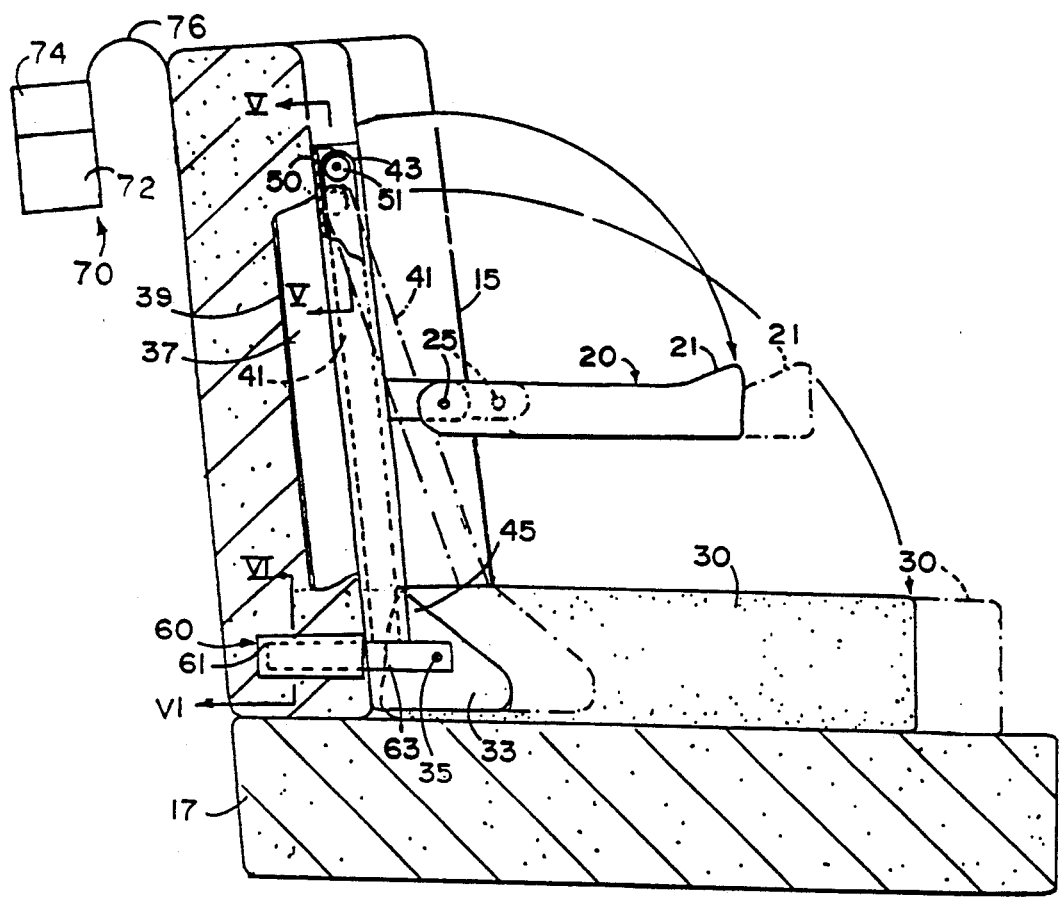
FIG. 3 is a side sectional view of the seat of FIG. 2.

Referring to the drawings in greater detail, a seating unit 10 of the present invention has a child restraint bar 20 and a child seat cushion 30 which are mounted with a frame 40 for folding into a closed position to become a part of an adult seat back 11 (FIGS. 1, 2 and 3).

Restraint bar 20 is a generally U-shaped member having legs 23. Bar 20 is built-up with safety padding and upholstery (FIGS. 1 and 2). A wedge portion 21 on bar 20 is built-up with an extra thickness of padding to provide added safety to a child by presenting a larger surface area and a deeper padding in an area where a child might contact the bar in a sudden stop or accident. Bar 20 is pivotally fastened to frame 40 at pivots 25 (FIG. 3), near the ends of legs 23. Bar 20 can pivot between an open horizontal position (FIG. 2) and a closed or stored vertical position (FIG. 1). In the open position, bar 20 surrounds a child using seating unit 10, restraining the child. The restraining properties of bar 20 are preferably supplemented by a typical child restraint harness (not shown). In the closed position bar 20 is folded into back 11 with an edge surface 27 below the top surface 13 of back 11, and a face surface 29 of bar 20 flush with a face surface 15 of back 11.

In such a construction of a high back style seat and the like, where bar 20 cannot practically extend so that edge surface 27 is flush with top surface 13 of back 11, a top cushion 70 is provided (FIGS. 1, 2 and 3). Cushion 70 fills an area 71 near the top of seat back 11, above stored bar 20 to provide a flush face surface 15 when seating unit 10 is stored and an esthetically pleasing flush top surface 13. Cushion 70 comprises a front portion 72 and a rear portion 74 connected to form a T- shaped top cushion 70. Cushion 70 is preferably attached to back 11 by a hinge connection. The hinge connection between cushion 70 and back 11 may simply comprise a strip of fabric 76 extending between the cushion and the back as shown (FIG. 2). When unit 10 is opened for use, cushion 70 is simply flipped over the top of back 11 so that the use of the child seat is not hindered by a restricting overhead structure.

Child seat cushion 30 also pivots between an open horizontal position (FIG. 2) and a closed vertical position (FIG. 1). Cushion 30 is pivotally attached at each side, near its lower edge 31, to frame 40 at pivots 35 (FIG. 3). A framing plate 33 is built into each side of cushion 30 near edge 31. Plates 33 pivot with cushion 30 and provide a foundation for pivotally connecting the cushion to frame 40.

Frame 40 has two vertical side braces 41 which are pivotally connected, near their upper end 43, to back 11 by vertical sliding tracks 50 (FIG. 5) so that the lower ends 45 of braces 41 can pivot away from back 11 and upper ends 43 of braces 41 can slide down the tracks 50. Tracks 50 are elongated channels having a "C" cross-section for retaining a slide, preferably a wheel 51, which in turn is pivotally connected to upper end 43 of side brace 41 by a stub axle 53.

Figures 4, 5, 6:
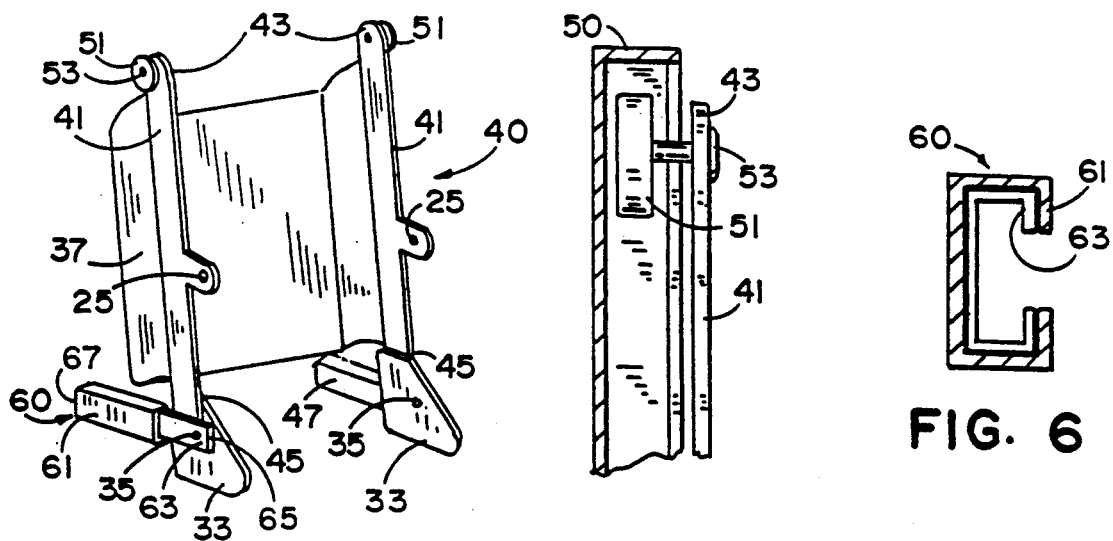
FIG. 4 is a perspective view of the structural framework of FIG. 2.
FIG. 5 is a sectional view along plane V—V of FIG. 3.
FIG. 6 is a sectional view along plane VI—VI of FIG. 3.

Lower ends 45 of braces 41 are pivotally connected at pivots 35 to one end of telescoping rods 60. An inner "C"-channel 61 is retained within an outer "C"-channel 63 (FIG. 6). Channel 61 slides within channel 63 to provide a telescoping action. Each channel 61 is pivotally connected at one end 65 to a plate 33 (FIG. 4). The opposing end 67 of each channel 63 is pivotally anchored in back 11. A child seat back foundation 37 extends between braces 41. Foundation 37 is located in a recess behind bar 20 and cushion 30. Further, foundation 37 is preferably made from a sheet of 16 gauge steel which is bent to form a two inch deep, open ended basket behind braces 41. Foundation 37 is preferably welded along each side to braces 41.

Figure 7:
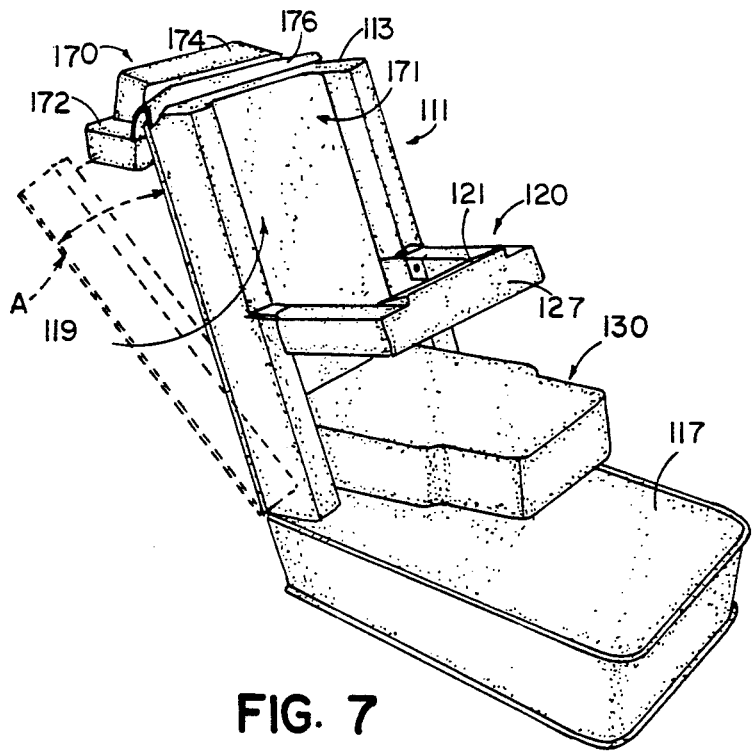
FIG. 7 is a perspective view of an alternative embodiment of a seat according to the invention in the open position.
Figures 8, 9:
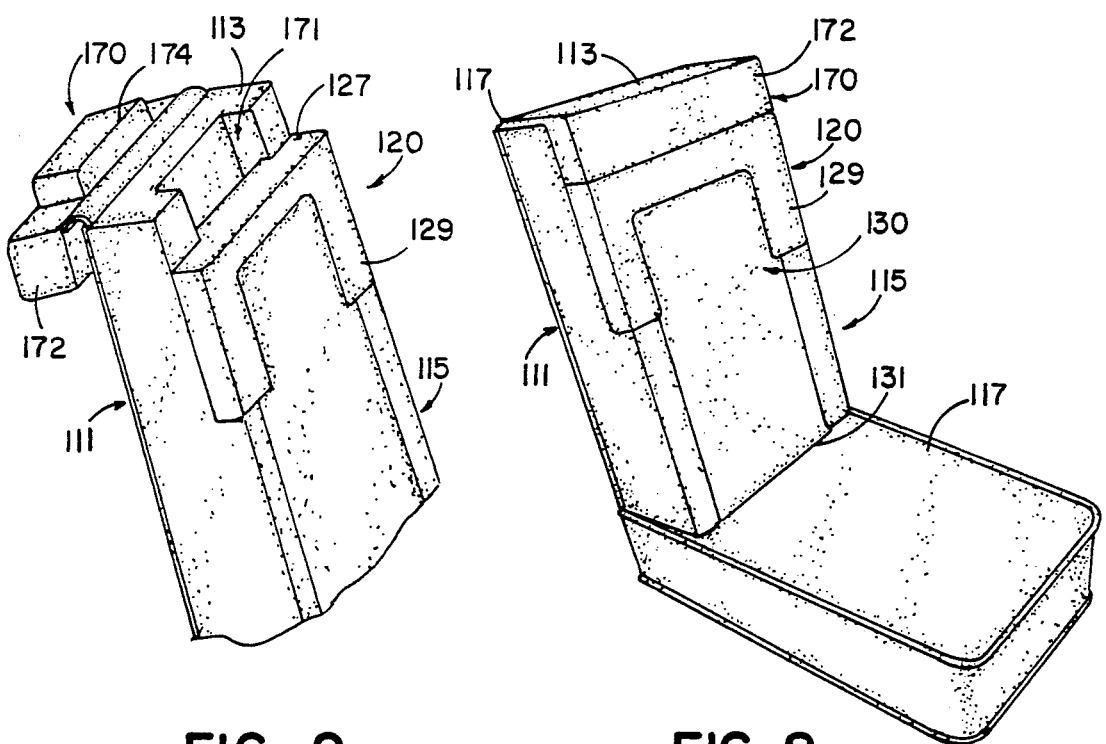
FIG. 8 is a perspective view of the seat of FIG. 7 in the closed position.
FIG. 9 is a fragmentary detail of the top of the seat of FIG. 8.

An alternative seat 110 which is very similar to the seat of FIGS. 1-6 as shown in FIGS. 7-9. Seat 110 includes a back 111 which can pivot backwardly to the position as disclosed by phantom lines "A" such as in a bus or airplane. In many such cases it is not necessary that a separate back support be pivoted independently of the back of the seat. Therefore, in FIGS. 7, 8 and 9, a separate, independently pivotable back support is not provided, merely an upholstered recessed area 119, formed in the back 111. In this modification, stationary frame members (not shown) similar to side frame members 41 of FIG. 4, are mounted in the back 111 on each side of the recess 119 and the cushion 130 and restraint bar 120 are pivotally mounted on this frame. In this construction, cushion 130 and restraint bar 120 are adapted to be pivoted upwardly or downwardly as disclosed in FIGS. 7 and 8, respectively. The inclination of the recessed back support is provided by the incline of the entire seat back 111. In order to accommodate larger children, a cushion 170 of essentially the same shape and construction of cushion 70 is pivotally mounted at the top edge of the seat by hinge 176 in a manner similar to that previously described in relation to cushion 70 of FIGS. 1-6. Cushion 170 is adapted to fill the void 171 or be flipped over the top of back 111 as disclosed in FIG. 7.

It should be understood that an extremely high back seat of this type may also include an independent pivotable back as disclosed in FIGS. 1-6 to provide independent tilting of a back support in addition to the tilting of the entire seat back 111.

OPERATION

In operation of the seat 10 of FIGS. 1-6, seating unit 10 is opened by pivoting cushion 30 forward about edge 31 until cushion 30 is in a horizontal position, laying on adult seat 17. Since cushion 30 and seat 17 are each fabricated from compliant upholstery material, each "gives" to allow cushion 30 to pivot forward to the open position. Restraint bar 20 is likewise opened by pivoting forward about pivots 25 until bar 20 is cantilevered forward in a horizontal position.

Cushion 70 is simply flipped over the top of back 11 (FIGS. 1, 2 and 3). An upholstered recessed area 19 is revealed in back 11 when bar 20 and cushion 30 are opened and forms the back for the child seat.

Cushion 30 is pulled forward and rods 60 telescope to adjust the incline of the child seat back. A child is placed between legs 23 of bar 20 to sit upon cushion 30. The child is preferably strapped into seat 10 with a typical child restraint harness (not shown).

In the operation of the seat 110 of FIGS. 7-9, the seating unit is opened by pivoting cushion 130 forward until cushion 130 is in a horizontal position as disclosed in FIG. 7. Restraint bar 120 is likewise opened by pivoting forward until bar 120 is cantilevered forward in a horizontal position as disclosed in FIG. 7.

The cushion 170 is then simply flipped over the top of the back 111. In the open position, as disclosed in FIG. 7, the cushion 130, restraint bar 120 and cushion 170 provide an upholstered recess area 119 in the back 111. The incline of the back can then be adjusted as is well known in the art of bus and airplane seats and the like.

While a preferred form of the invention has been shown and described, other forms will now be apparent to those skilled in the art. Therefore, it will be understood that the embodiments shown in the drawings and described above are merely for illustrative purposes, and are not intended to limit the scope of the invention which is defined by the claims which follow.

The embodiments of the invention in which an exclusive property or privilege is claimed are defined as follows.

1. A child restraint seat comprising:
    a first back portion of an adult seat back which can be separated from the remainder of said back, has a lower end, has an upper end and can rotate about said lower end between a closed position wherein said first back portion is nestled flush within said adult seat back to provide a part of the back support for an adult and an open position wherein said first back portion extends generally horizontally forward from said adult seat back to provide a seat for a child;
    a second back portion of said adult seat back which can be separated from the remainder of said adult seat back has an inverted U-shape with two legs extending generally downwardly from a bight portion, each leg having a lower end, and can be rotated about said lower ends between a closed position wherein said second back portion partially circumscribes said upper end of said first back portion, when in its closed position, and is nestled flush within said adult seat back to provide a part of the back support for an adult and an open position wherein said second back portion extends generally horizontally forward from said back to provide a restraint bar for a child;

a third back portion of said adult seat back which can be separated from the remainder of said adult seat back, extends generally upwardly from said second back portion, has a top surface defining at least a part of a top surface of said adult seat back, is nestled flush within said adult seat back in a closed position to provide a part of the back support for an adult and reveals a void along the upper edge of said adult seat back in an open position for accommodating the upper part of a tall child; and a child seat back which is located behind said first, second and third back portions, concealed when each of said back portions is in its respective closed position and revealed for receiving and supporting the back of a child when said back portions are in their respective open positions.

2. The seat defined in claim 1 in which said child seat back includes frame means for inclining said child seat back when said first and second back portions are in their respective open positions.

3. The seating unit of claim 2 wherein said frame means includes:

a first vertical side member which has an upper end attached within said adult seat back near said top surface, can be rotated about said upper end, has a lower end attached to a first side of said lower end of said first back portion and has a midportion to which one of said two legs of said second back portion is attached at said lower end of said leg; and a second vertical side member, which is generally parallel to said first member, has an upper end attached within said adult seat back near said top surface, can be rotated about said upper end, has a lower end attached to the other side of said lower end of said first back portion and has a midportion to which the other of said two legs of said second back portion is attached at said lower end of said leg.

4. The seating unit of claim 3 wherein:

said frame means further includes a foundation means for supporting said child seat back, said foundation means extending between said first and second side members; and said adult seat back further includes means defining a recess for receiving said foundation means when said seating unit is closed.

5. The seating unit of claim 4 wherein:

each said upper end of said vertical side members is attached to a fastening means within said adult seat back which can slide vertically; and said frame means further includes:

a first horizontal side member which is located generally in a first reference plane which is substantially perpendicular to said adult seat back, has a first end fastened within said adult seat back, and has a second end which can telescope to effectively extend the length of said member, said second end being attached to said first side of said first back portion at said lower end; and a second horizontal side member which is located generally in a second reference plane, said second reference plane being substantially parallel to said first reference plane, has a first end fastened within said adult seat back, and has a second end which can telescope to effectively extend the length of said member, said second end being attached to said other side of said first back portion at said lower end.

6. A seat back portion of an adult seating unit, said back having a child restraint seat convertible from a stored position within said back to an open position for holding and restraining a child, comprising:

an adult seat back having a top edge, bottom edge and front face surface;

said adult seat back including a child seat cushion which extends generally upwardly from said bottom edge of said adult seat back in a stored position, can be separated from the remainder of said adult seat back, has a lower end, has an upper end and can rotate about said lower end between said stored position wherein said seat cushion is nestled within said adult seat back and flush with said front face to provide a part of the back support for an adult and an open position wherein said seat cushion extends generally horizontally forward from said adult seat back to provide a seat for a child;

said adult seat back further including a child restraint bar which can be separated from the remainder of said adult seat back, generally has an inverted U-shape with two legs extending generally downwardly from a bight portion in a stored position, each leg having a lower end, and can rotate about said lower ends between said stored position wherein said restraint bar partially circumscribes said upper end of said seat cushion when in its stored position, is nestled within said adult seat back and is flush with said front face surface to provide a part of the back support for an adult and an open position wherein said restraint bar extends generally horizontally forward from said adult seat back;

said adult seat back further including a top cushion which can separate from the remainder of said adult seat back, extends generally upwardly from said child restraint bar, has a top surface defining at least a portion of said top edge of said adult seat back, is nestled within said adult seat back and is flush with said front face surface in a stored position and can be positioned so that a void is provided along said top edge of said adult seat back in an open position;

said adult seat back further including a child back support which is generally located and concealed behind said child seat cushion, restraint bar and top cushion, when each is in its respective stored position, and is generally exposed for receiving and supporting a child when each of said child seat cushion, restraint bar and top cushion is in its respective open position.

7. The seat back of claim 6 wherein said adult seat back is pivotable about said lower end for reclining said adult seat back and for reclining said child back support to receive and support a child in a reclined position.

8. The seat back of claim 6 in which said child back support includes frame means for inclining said child seat back support.

9. The seat back of claim 8 wherein said frame means includes:

a pair of vertical side members which are positioned and spaced in a generally parallel relation to each other within said adult seat back, have upper ends rotatably attached within said back near said top surface, have lower ends attached to said child seat cushion near said lower end and have midportions to which said lower ends of said legs of said restraint bar are attached;

foundation means extending between and attached to said vertical side members for supporting said child seat back support;

a pair of horizontal side members located within said adult seat back and positioned generally perpendicularly to said front face, said horizontal side members having first ends fastened within said back and second ends which can telescope to effectively lengthen each said horizontal side member, said second ends being attached to said child seat cushion at said lower end.

10. The seat back of claim 9 wherein said adult seat back further includes means defining a recessed area behind said child seat back support for receiving said foundation means when said child restraint seat is in said stored position.

11. An adult seating unit which is convertible to a child restraint seat, comprising:

an adult seat portion having a generally horizontal and upwardly facing support surface for receiving and supporting a person sitting thereon;

an adult portion having a top edge, bottom edge and front surface;

a child seat cushion which is nestled within said adult back and flush with said front surface in a stored position to provide a part of the back support for an adult, extends generally upwardly from said bottom edge of said adult back in said stored position, can separate from the remainder of said adult back, has a lower end, has an upper end and can rotate about said lower end between said stored position and an open position wherein said seat cushion extends generally horizontally forward from said adult back to provide a seat for a child;

a child restraint bar which is nestled within a said adult back and is flush with said front surface in a stored position to provide a part of the back support for an adult, can separate from the remainder of said adult back, has an inverted generally U-shape with two legs extending generally downwardly from a bight portion in said stored position, each leg having a lower end, can rotate about said lower ends between said stored position wherein said restraint bar partially circumscribes said upper end of said seat cushion when said seat cushion is in its stored position and an open position wherein said restraint bar extends generally horizontally forward from said adult seat back;

a top cushion which is flush with said front surface in a stored position, can separate from the remainder of said adult back, has a top surface defining at least a portion of said top edge of said adult back, extends generally between said top surface and said restraint bar and provides an unobstructed void along said top edge of said adult back in an open position;

a child back support which is located behind and concealed by said child seat cushion, restraint bar and top cushion when each is in its respective stored position, is generally exposed for receiving and supporting a child when each of said child seat cushion, restraint bar and top cushion is in its respective open position and can separate from the remainder of said adult back to provide an inclined back support for a child; and means defining a recess in said adult back for receiving said child back support when said child restraint seat is in its stored position.

12. The seat back of claim 11 wherein said adult back portion is pivotable about said bottom edge for reclining said adult back portion and for reclining said child back support to receive and support a child in a reclined position.

13. The seat back of claim 11 in which said child back support includes frame means for inclining said child seat back support.

14. The seat back of claim 13 wherein said frame means includes:

a pair of vertical side members which are positioned and spaced in a generally parallel relation to each other within said adult seat back, have upper ends rotatably attached within said back near said top surface, have lower ends attached to said child seat cushion near said lower end and have midportions to which said lower ends of said legs of said restraint bar are attached;

foundation means extending between and attached to said vertical side members for supporting said child seat back support;

a pair of horizontal side members located within said adult seat back and positioned generally perpendicularly to said front face, said horizontal side members having first ends fastened within said back and second ends which can telescope to effectively lengthen each said horizontal side member, said second ends being attached to said child seat cushion at said lower end.

15. The seat back of claim 14 wherein said top cushion is attached to said adult back by a hinge connection means so that said top cushion can be hinged over the top of said adult back between said stored position and said open position.

16. A child restraint seat comprising:

a first portion of an adult seat back, said first portion being pivoted at its lower end to be separable from the remainder of said adult seat back and being movable between a closed position wherein said first portion is nestled flush within said adult seat back to provide a part of the back support for an adult and an open position wherein said first portion extends generally horizontally forward from said adult seat back to provide a seat for a child;

a second portion of said adult seat back, said second portion being separable from the remainder of said adult seat back, and being movable between a closed position wherein said second portion is nestled flush within said adult seat back to provide a part of the back support for an adult and has a top surface defining at least a part of a top surface of said adult seat back and an open position wherein a void along the upper edge of said adult seat back is revealed for accommodating the upper part of a tall child, said second portion being hingedly attached to said adult back to pivot upwardly into said open position to create said void along the upper edge of said adult seat back; and a child seat back located behind said first and second back portions for receiving and supporting a child when said first and second portions are in their respective open positions.

17. The seat defined in claim 16 in which said child seat back includes frame means for inclining said child seat back.

18. The seating unit of claim 17 wherein said frame means includes:
- a first vertical side member having an upper end rotatably attached within said adult seat back near said top surface and having a lower end attached to a first side of said first back portion; and
- a second vertical side member, generally parallel to said first member, having an end rotatably attached within said adult seat back near said top surface and having a lower end attached to a second side of said first back portion, said second side being opposite said first side.

19. The seating unit of claim 18 wherein:
said frame means further includes a foundation means for supporting said child seat back, said foundation means extending between said first and second side members; and
said adult seat back further includes means defining a recess for receiving said foundation means.

20. The seating unit of claim 18 wherein:
said upper end of each said first and second vertical side member is connected with a generally vertically slidable fastening means within said adult seat back; and
said frame means further includes:
- a first horizontal side member, located generally in a first reference plane, said first reference plane being substantially perpendicular to said adult seat back, having a first end fastened within said adult seat back, and having a second end which telescopes to effectively change the length of said member, said second end being attached to said first side of said first back portion; and
- a second horizontal side member, located generally in a second reference plane, said second reference plane being substantially parallel to said first reference plane, having a first end fastened within said adult seat back, and having a second end which telescopes to effectively change the length of said member, said second end being attached to said second side of said first back portion.

21. A seat back portion of an adult seating unit, said back having a child restraint seat convertible from a concealed position within said back to an open position for holding and restraining a child, comprising:
- an adult seat back having a top edge, bottom edge and front face surface;
- said adult seat back including a child seat cushion which extends generally upwardly from said bottom edge of said adult seat back in a concealed position, can be separated from the remainder of said adult seat back, has a lower end, and can rotate about said lower end between said concealed position wherein said seat cushion is nestled within said adult seat back and is flush with said front face to provide a part of the back support for an adult and an open position wherein said seat cushion extends generally horizontally forward from said adult seat back to provide a seat for a child;
- said adult seat back further including a top cushion which can separate from the remainder of said adult seat back, has a top surface defining at least a portion of said top edge of said adult seat back, is nestled within said adult seat back, is flush with said front face surface in a concealed position, and can be positioned so that a void is provided along said top edge of said adult seat back in an open position;
- means for pivotally attaching said top cushion to said adult back by a connection means so that said top cushion pivots upwardly from said stored position and to said open position wherein a void along the upper edge of said adult seat back is revealed for accommodating the upper part of a tall child; and
- said adult seat back further including a child back support which is generally located behind said child seat cushion and said top cushion and is generally exposed for receiving and supporting a child when each of said child seat cushion and top cushion is in its respective open position.

22. The seat back of claim 21 wherein said adult seat back is pivotable about said lower end for reclining said adult seat back and for reclining said child back support to receive and support a child in a reclined position.

23. The seat back of claim 21 in which said child back support includes frame means for inclining said child seat back support.

24. The seat back of claim 23 wherein said frame means includes:
- a pair of vertical side members which are positioned in generally spaced and parallel relation to each other, are located within said adult seat back, have upper ends rotatably attached near said adult seat back top edge, and have lower ends attached to said child seat cushion near said lower end;
- foundation means extending between and attached to said vertical side members for supporting said child seat back support; and
- a pair of horizontal side members located within said adult seat back and positioned generally perpendicularly to said front face surface, said horizontal side members having first ends fastened within said back and second ends which telescope to effectively change the length of each said horizontal side member, said second ends being attached to said child seat cushion near said lower end.

25. The seat back of claim 24 wherein said adult seat back further includes means defining a recessed area behind said child seat back support for receiving said foundation means.

26. An adult seating unit which is convertible to a child restraint seat, comprising:
- an adult seat portion for receiving and supporting a person sitting thereon;
- an adult back portion having a top edge, bottom edge and front surface;
- a child seat cushion which is nestled within said adult back and flush with said front surface in a stored position to provide a part of the back support for an adult, extends generally upwardly from said bottom edge of said adult back in said stored position, can separate from the remainder of said adult back, has a lower end, has an upper end, and can rotate about said lower end between said stored position and an open position wherein said seat cushion extends generally horizontally forward from said adult back to provide a seat for a child;
- a top cushion which is flush with said front surface in a stored position, can separate from the remainder of said adult back, has a top surface defining at least a portion of said top edge of said adult back, and provides an unobstructed void along said top edge of said adult back in an open position;
- said top cushion being attached to said adult back by a hinge connection means so that said top cushion hinges over the top of said adult back between said stored position and said open position;

a child back support which is located behind said child seat cushion and said top cushion and is generally exposed for receiving and supporting a child when each of said child seat cushion and said top cushion is in its respective open position; and means defining a recess in said adult back in which said child back support is located.

27. The seat back of claim 26 wherein said adult back portion is pivotable about said bottom edge for reclining said adult back portion and for reclining said child back support to receive and support a child in a reclined position.

28. The seat back of claim 26 in which said child back support includes frame means for inclining said child seat back support.

29. The seat back of claim 28 wherein said frame means includes:

a pair of vertical side members which are positioned in generally spaced and parallel relation to each other, are located within said adult seat back, have upper ends rotatably attached near said adult back top edge, and have lower ends attached to said child seat cushion near said lower end;

foundation means extending between and attached to said vertical side members for supporting said child seat back support; and a pair of horizontal side members located within said adult back and positioned generally perpendicularly to said front surface, said horizontal side members having first ends fastened within said adult back and second ends which telescope to effectively change the length of each said horizontal side member, said second ends being attached to said child seat cushion near said lower end.

30. A seat assembly comprising a child restraint seat integrated into an adult seat assembly comprising:

said adult seat assembly including an adult seat and an adult seat back, said adult seat back having at least first and second portions, said first portion being located at the lower end of said adult seat back and said second portion being located at the upper end of said adult seat back, said first portion being separable from the remainder of said adult seat back and being pivoted at its lower end so as to be movable between a closed position wherein said first portion is nestled flush with said adult seat back to provide a part of the back support for an adult and an open pivoted position wherein said first portion extends generally horizontally forward from the adult seat back to provide a seat for a child;

said second portion of said adult seat back being pivotally movable upwardly between a closed position wherein said second portion in a closed position is nestled flush with said adult seat back to define at least a part of the back support for an adult and at least a part of the top surface of said adult seat back and in an open position creating a void along the upper edge of said adult seat back for accommodating the upper part of a tall child; and a child seat back located behind said second back portions for receiving and supporting a child when the first and second portions are in their respective open positions.

* * * * *

UNITED STATES PATENT AND TRADEMARK OFFICE
CERTIFICATE OF CORRECTION

PATENT NO. : 5,100,199
DATED : March 31, 1992
INVENTOR(S) : Louis M. VanderStel et al.

It is certified that error appears in the above-identified patent and that said Letters Patent is hereby corrected as shown below:

Column 9, claim 18, line 8:
　　After "an" insert --upper--.

Signed and Sealed this

Ninth Day of November, 1993

Attest:

BRUCE LEHMAN

Attesting Officer　　　Commissioner of Patents and Trademarks